US008400470B2

(12) United States Patent
Shields et al.

(10) Patent No.: US 8,400,470 B2
(45) Date of Patent: Mar. 19, 2013

(54) CLIENT SIDE MULTI-COMPONENT IMAGE COMPOSITION

(75) Inventors: Kevin Shields, Whitley Bay (GB);
James Raine, South Shields (GB);
Gavin Hope, Gateshead (GB)

(73) Assignee: Genetix Corp, San Jose, CA (US)

( * ) Notice: Subject to any disclaimer, the term of this patent is extended or adjusted under 35 U.S.C. 154(b) by 865 days.

(21) Appl. No.: 12/196,199

(22) Filed: Aug. 21, 2008

(65) Prior Publication Data

US 2010/0045698 A1 Feb. 25, 2010

(51) Int. Cl.
*G09G 5/00* (2006.01)
(52) U.S. Cl. ........................ 345/629; 345/630
(58) Field of Classification Search ........................ None
See application file for complete search history.

(56) References Cited

U.S. PATENT DOCUMENTS

| 6,017,157 | A  | * | 1/2000  | Garfinkle et al. ............. 396/639 |
| 7,565,441 | B2 | * | 7/2009  | Romanik et al. ............. 709/234 |
| 2002/0044696 | A1 |   | 4/2002  | Sirohey et al. |
| 2004/0218818 | A1 |   | 11/2004 | Clare et al. |
| 2004/0230613 | A1 |   | 11/2004 | Goldstein et al. |
| 2005/0002547 | A1 |   | 1/2005  | Torre-Bueno |

FOREIGN PATENT DOCUMENTS

| FR | 2 854 525 A1 | 5/2004 |
| WO | WO 01/59706 A1 | 8/2001 |

OTHER PUBLICATIONS

European Search Report from EP 09251857.0, dated Dec. 18, 2009 (5 pages).
Franti et al.; "Compression of map images for real-time applications"; *Image and Vision Computing* 22(13): 1105-1115 (Nov. 2004).
Lin et al.; "3D Model Streaming Based on JPEG 2000"; *IEEE Transactions on Consumer Electronics* 53(1): 182-190 (Feb. 2007).
Panchanathan et al.; "Wavelet Based Scalable Image Compression"; *SPIE*; 2419: 505-514 (Feb. 1995).
Smith et al.; "Content-based transcoding of images in the Internet"; 1998 International Conference on Image Processing (ICIP '98), IEEE Comp. Soc., vol. 3, pp. 7-11, in Chicago, IL, Oct. 4-7, 1998.

* cited by examiner

*Primary Examiner* — M Good Johnson
(74) *Attorney, Agent, or Firm* — Kilpatrick Townsend & Stockton LLP

(57) ABSTRACT

A method is provided for displaying a client-side multi-component image. A plurality of image component channels derived from captured images of a sample are stored in a server, the plurality of image component channels being stored in the form of a plurality of image data records. A client then requests one or more of the plurality of image data records and the server transmits to the client the one or more of the plurality of image data records requested. At the client, the client-side multi-component image is composited from the image data records transmitted the composited client-side multi-component image is displayed.

20 Claims, 12 Drawing Sheets
(3 of 12 Drawing Sheet(s) Filed in Color)

CLIENT SIDE MULTI-COMPONENT IMAGE COMPOSITION

BACKGROUND OF THE INVENTION

The present invention relates to tissue sample analysis and imaging. More particularly, but not exclusively, this invention relates to digital images for telepathology being accessed on a storage server by a remote client.

DESCRIPTION OF THE PRIOR ART

Digital imaging systems are now commonly used for the acquisition and analysis of images of tissue samples and cell mono-layers. Systems such as Ariol® produced by Applied Imaging/Genetix have been developed for the digital capture of both bright field and fluorescent images, as well as the automated quantitative analysis of immunohistochemistry-(IHC) and fluorescent in situ hybridization-(FISH) labeled samples.

In such a system high resolution digital image data and associated meta-data (labels, regions of interest and so on) are stored. The digital image data may comprise multiple component channels, for example both bright field and multiple fluorescent labeled images, derived from a given sample.

At the same time, it is common for data generated by one computing system to be made available to another computing system. This remote access of data might for example take place across a relatively short physical distance, such as between two computers in a hospital intranet, or could happen over much larger distances via the internet, such as between a laboratory server in one country and an expert pathologist located in a different country.

In a high bandwidth network, such as a hospital picture archiving and communications systems (PACS) network, it will be possible to transmit image files in their native or raw form from a server to a client. The client may then run applications locally to process and/or analyze the image files as desired. However in a lower specification network, for example over the internet or over a standard LAN (local area network), the image files may be too large for this to be feasible and in this situation the arrangement of server and client is often such that, in order to reduce the required communication bandwidth between the server and client, as little information as possible is transferred from the server to the client. For example application software generating the image to be displayed may be executed on the server and only necessary display information for the client user is transmitted to the client. This is known as a "thin client" approach.

However, it is also known for such remote access to be configured such that the client may interact with the server such that, as well as requesting particular images or information from the server, the client may actively cause processing to happen at the server. Systems such as those provided by Citrix® Systems can provide the resources for this variety of interaction to occur.

Nevertheless, despite improvements in intranet and internet infrastructures, the high resolution at which digital images may now be produced by imaging systems such as those mentioned above means that bandwidth constraints remain a significant hurdle in the development of these client-server systems. Whilst image compression techniques (such as JPEG) are capable of reducing the size of the data files that are transmitted from server to client, the consequent loss of image quality is an undesirable side effect. US 2005/0002547 discloses one such image compression technique in the context of medical imaging.

Consequently, it would be desirable to provide an improved technique for arranging such a client-server systems, such that the client side user may benefit from the advantages of remote access to server-stored digital imaging data, whilst improving the quality of the images with which the client user is presented.

BRIEF SUMMARY OF THE INVENTION

Viewed from a first aspect, the present invention provides a method of displaying a client-side multi-component image, comprising:

storing in a server a plurality of image component channels derived from captured images of a sample, said plurality of image component channels being stored in the form of a plurality of image data records;

requesting by a client one or more of said plurality of image data records;

transmitting from the server to the client the one or more of said plurality of image data records requested in said requesting step;

compositing the client-side multi-component image from the one or more of said plurality of image data records transmitted in said transmitting step; and displaying the composited client-side multi-component image.

Typically, in the prior art, the problem of limited network bandwidth has been addressed by the compression of the image to be displayed at the client side before transmission from the server to the client. This technique inherently involves a trade-off between greater compression (and hence smaller file size) and the consequent reduction in image quality. However, this approach brings further limitations when applied to multi-component images, since conventional image file compression protocols are based on and applied to 3-channel (e.g. RGB) images. This means that when a composited multi-component image, for example a 5-component image, is compressed it is only its RGB image which is compressed and transmitted to a client machine. As a consequence, the client is unable to retrieve the original multiple components of the image, since the distinct separate channel information has been lost in the compression process.

The inventors of the present invention, however, realized that the client could be provided with a more flexible system, in which the separate channel information is retained by storing in the server a plurality of image data records, the image data records representing component channels derived from the captured images. The client can then request only those channels which are of interest, thus saving transmission bandwidth. The component channels are then composited at the client to form a client-side multi-component image, which is then displayed. Significantly, the client then has the opportunity to reconfigure the displayed image, for example by toggling one component channel on and off, to more accurately view the contribution of that particular component channel to the displayed image.

In one embodiment, the plurality of image data records comprises a hierarchy of image data records for each component channel, each hierarchy comprising a set of image data records, each set of image data records comprising image data records having different resolutions from each other; the method further comprising:

at said requesting step the client specifying a desired resolution; and at said transmitting step the server selecting and transmitting image data records appropriate to the desired resolution that has been requested.

It will be understood that the desired resolution may be requested directly or indirectly by the client, and the above wording covers both possibilities. In typical use, the user at the client side will issue commands to the client machine in terms of the extent of a viewing window. The client machine may translate that into a desired resolution, and transmit that as a request to the server machine, so that the client directly requests a desired resolution. Alternatively, the client machine may simply pass to the server machine the viewing window coordinates, and leave it to the server to translate this information into a desired resolution, so that the client is indirectly requesting a desired resolution.

In this manner the bandwidth requirements of the system may be further reduced, since for each component channel the server stores a hierarchy of image data records with the levels in the hierarchy representing points in a range of resolutions. The user at the client can then, for example initially, request only low resolution versions of the selected component channels to get an overview of the captured images, then later requesting higher resolution versions to examine the images in more detail, either directly or indirectly as discussed above.

In one embodiment, the plurality of image data records comprises a set of tiles for each image component channel, the set of tiles together forming the image component channel; the method further comprising:

at said requesting step specifying a desired portion of the captured images; and at said transmitting step transmitting image data records appropriate to the desired portion of the captured images.

In this manner the bandwidth requirements of the system may be further reduced, since a set of tiles makes up each image component channel derived from the captured images. The user at the client can then request only those areas of the selected component channels that are of interest, corresponding to one particular region of the captured images.

In the event that the user requests more than one tile, then in one embodiment said compositing further comprises stitching more than one tile of said set of tiles together to form the composited client-side multi-component image. Thus the client user may be presented with a conveniently presented image composed of a selection of tiles of interest, stitched together to present a single image covering the area of those tiles. Furthermore the client user may pan across the composited client-side multi-component image, further tiles that are required to complete portions of the image coming into view only being retrieved from the server when they are required for display.

In one embodiment, said plurality of image data records comprises image data records corresponding to different focal depths of the captured images, the method further comprising:

at said requesting step the client specifying a desired focal depth of the captured images; and at said transmitting step the server transmitting image data records appropriate to the desired focal depth of the captured images.

Due to the fact that a sample under investigation will typically have a finite depth, depending on the magnification at which the images are being captured and the nature of the sample it can be advantageous for images of the sample to be captured as images at a range of focal depths. In the context of pathology at least, such image data sets are referred to as z-stacked data sets. The client user may then examine the range of focal depth images to determine the focal depth at which the image is most clearly viewable and/or useful for analysis. Alternatively this determination may be carried out by software analysis, for example by contrast analysis, maximum intensity projection, or SUM or X-ray projection which are all well known techniques in imaging, in particular medical imaging.

In one embodiment, the image component channels of the captured images are monochromatic. In this manner the bandwidth requirements of the system may be further reduced, since for each image component channel no color information need be stored or transmitted.

The storing step may beneficially comprise compressing the captured images into the image data records using an image data compression protocol, for example taken from: JPEG, JBIG, PNG, WBMP, BMP, GIF, ICER, ILBM, PCX, PGF, TGA and TIFF, so that each image data record includes a compressed version of the captured images. The image data records may in parallel include un-compressed, so-called raw, versions of the same image component channels, or the compressed versions may be the only ones stored.

It will be appreciated that JPEG, JBIG, PNG, WBMP, BMP, GIF, ICER, ILBM, PCX, PGF, TGA and TIFF is a non-exhaustive list provided by way of example only. It will be understood that the invention may be applied to other existing data formats, as well as data formats developed in the future.

A key advantage of this approach in the context of a narrow or limited bandwidth communication between client and server, such as a low specification LAN network, or an internet connection, is that the user at the client side retains the freedom to toggle between viewing different combinations of image component channels in the client side display, but it is only necessary to transmit from the client to the server a compressed version of each image component channel. This approach is to be contrasted with the prior art approach of transmitting a compressed version of an RGB image of the already-composited image component channels over the network channel. The approach of the server transmitting each image component channel individually in compressed form to the client means that the user at the client side can adjust which combination of image component channels are composited at the client side without having to retransmit the composited image over the network each time the combination of image component channels to be viewed is changed by the user. All that is required is that a compositor is present on the client to perform the compositing function. This need only be a very primitive piece of applications software capable of combining the different image component channels. A full blown renderer is not required. The applications software may be permanently resident on the client, or supplied on demand by the server to the client as a downloadable component.

Those skilled in the art will recognize that there are a variety of ways in which the image component channels received at the client could be rendered for display, but in one embodiment the compositing step comprises transforming the one or more of said plurality of image data records transmitted in said transmitting step into an RGB image. There are clearly a number of formats, in particular space-saving compressed image formats, in which the client-side multi-component image could be produced. In embodiments of the present invention the compositing step comprises transforming the one or more of said plurality of image data records transmitted in said transmitting step into a compressed image format, for example taken from: JPEG, JBIG, PNG, WBMP, BMP, GIF, ICER, ILBM, PCX, PGF, TGA and TIFF.

It will be appreciated that the captured images could take a variety of forms. In one embodiment, the captured images are images of a tissue sample. In another embodiment, the captured images are images of a cell mono-layer. Whilst both of these embodiments will typically involve two-dimensional (2D) data, from which a 2D composited client-side multi-component image is generated, these could equally involve three-dimensional (3D) data, such as that from a tomographic scan, which could then be rendered in 2D on a display screen, or in 3D as a holographic display.

It will be appreciated that the image component channels of the captured images could derive from a range of sources. However in one embodiment, the image component channels of the captured images include fluorescent imaging information, either exclusively or in combination with other channels, for example a bright field image channel, a dark field image channel and/or one or more synthetic image channels derived from intermediate image processing of the raw acquired image data. This fluorescent imaging information could for example result from a fluorescent in situ hybridization (FISH) labeled sample or from an immunohistochemistry labeled sample.

In addition to information originally captured in the captured images, it is advantageous that the image component channels of the captured images comprise analysis data created after capturing of the captured images. In this manner analysis data, such as a mask indicating regions of interest in the image may also be selectively downloaded by the user. In some embodiments the analysis data is user-generated, such as a user-drawn contour enclosing a region of interest. In other embodiments the analysis data is software-generated, such as graphical information derived from software-based counting of features in the image.

In another embodiment, analysis may be performed at the client-side and the results of that analysis then up-loaded to the server, the method in this embodiment comprising the further steps of:

performing image analysis at the client;

generating additional image information at the client dependent on the image analysis; and uploading the additional image information as a further image data record to be stored in the server.

The additional image information may be stored at the server as text or other non-image data, for example in a file header, or may be stored as further image data, for example an extra image component channel to be stored with the other pre-existing image component channels for that sample, or as a combination of both.

In this manner, analysis data generated by a particular client user may be stored with its associated captured image(s) on the server, such that it is available for later viewing in association with the captured image(s) either by the same user, or by a different user, possibly at a different client machine. Thus the original user may return to some analysis results at a later point in time, or alternatively another user may examiner those analysis results, for example to give a second opinion.

Viewed from a second aspect, the present invention provides a client apparatus, the client apparatus configured to:

request from a server one or more of a plurality of image data records stored in the server, the plurality of image data records representing image component channels derived from captured images of a sample;

receive the one or more of said plurality of image data records transmitted from the server;

composite a client-side multi-component image from the one or more of said plurality of image data records transmitted from the server; and display the composited client-side multi-component image.

Viewed from a third aspect, the present invention provides a server apparatus, the server apparatus configured to:

store a plurality of image component channels derived from captured images of a sample, said plurality of image component channels being stored in the form of a plurality of image data records;

receive a request from a client for one or more of said plurality of image data records; and transmit to the client the one or more of said plurality of image data records requested.

Viewed from a fourth aspect, the present invention provides a system for displaying a client-side multi-component image, the system comprising:

a client apparatus and a server apparatus, the client apparatus configured to:

request from a server one or more of a plurality of image data records stored in the server, the plurality of image data records representing image component channels derived from captured images of a sample;

receive the one or more of said plurality of image data records transmitted from the server apparatus;

composite a client-side multi-component image from the one or more of said plurality of image data records transmitted from the server apparatus; and display the composited client-side multi-component image;

and the server apparatus configured to:

store the plurality of image component channels in the form of a plurality of image data records;

receive a request from the client apparatus for the one or more of said plurality of image data records; and transmit to the client apparatus the one or more of said plurality of image data records requested.

a client apparatus, the client apparatus configured to:

request from a server one or more of a plurality of image data records stored in the server;

receive the one or more of said plurality of image data records transmitted from the server;

composite a client-side multi-component image from the one or more of said plurality of image data records transmitted from the server; and display the composited client-side multi-component image.

BRIEF DESCRIPTION OF THE DRAWINGS

The patent or application file contains at least one drawing (i.e., FIGS. 10-12) executed in color. Copies of this patent or patent application publication with color drawing(s) will be provided by the Office upon request and payment of the necessary fee.

The present invention will be described further, by way of example only, with reference to embodiments thereof as illustrated in the accompanying drawings, in which.

DETAILED DESCRIPTION OF THE INVENTION

Figure 1A:
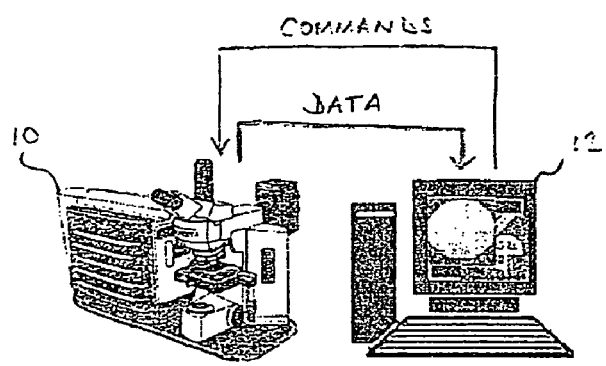
FIG. 1A schematically illustrates a microscope system for capturing images of a sample.

FIG. 1A schematically illustrates a microscope system for capturing images of a sample. The microscope unit 10 captures digital images of a sample under investigation and the digital images are transferred to computer 12 where they are stored. The microscope unit 10 can illuminate with white light for the capturing of bright field digital images, and can also illuminate with a range of specific wavelengths by means of a filter set for the excitation of particular fluorescent emissions.

In some embodiments the slide holding the sample may be loaded manually by a user, but in the illustrated example the microscope unit 10 comprises a set of microscope slide racks and an automated slide loader, so that a series of slides may be selected, positioned under the microscope, imaged and returned to the slide racks.

Furthermore, in the illustrated embodiment the computer 12 sends commands to the microscope unit 10 dictating which slides should be imaged, what magnifications they should be imaged at, which light source should be used to illuminate each slide, and so on. Once a series of captured images has been transferred from microscope unit 10 to computer 12, a user operating computer 12 may then examine those images, perform analysis on them, and so on. The example system illustrated is the Ariol® imaging system produced by Applied Imaging/Genetix.

Figure 1B:
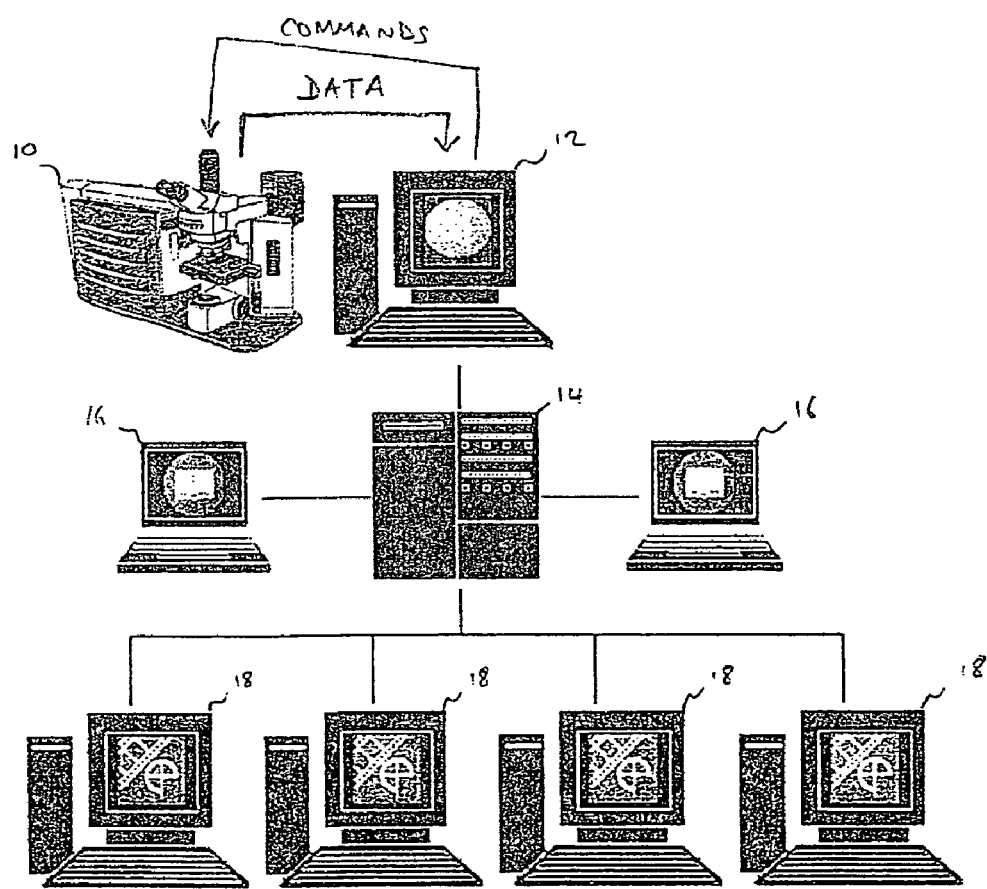
FIG. 1B schematically illustrates the microscope system of FIG. 1A connected to a server and network.

FIG. 1B schematically illustrates the microscope system of FIG. 1A connected to a server 14 and a network. The network consists of both computing devices 16 connected locally to the server 14, and of computing devices 18 located remote from the server 14, for example in a local area network (LAN) or via the internet. In the arrangement illustrated in FIG. 1B the captured images taken by microscope unit 10 are uploaded from computer 12 to the server 14, such that any of the other computing devices 16 or 18 connected to the server 14 may also view those captured images, perform analysis on them etc.

Figure 2:
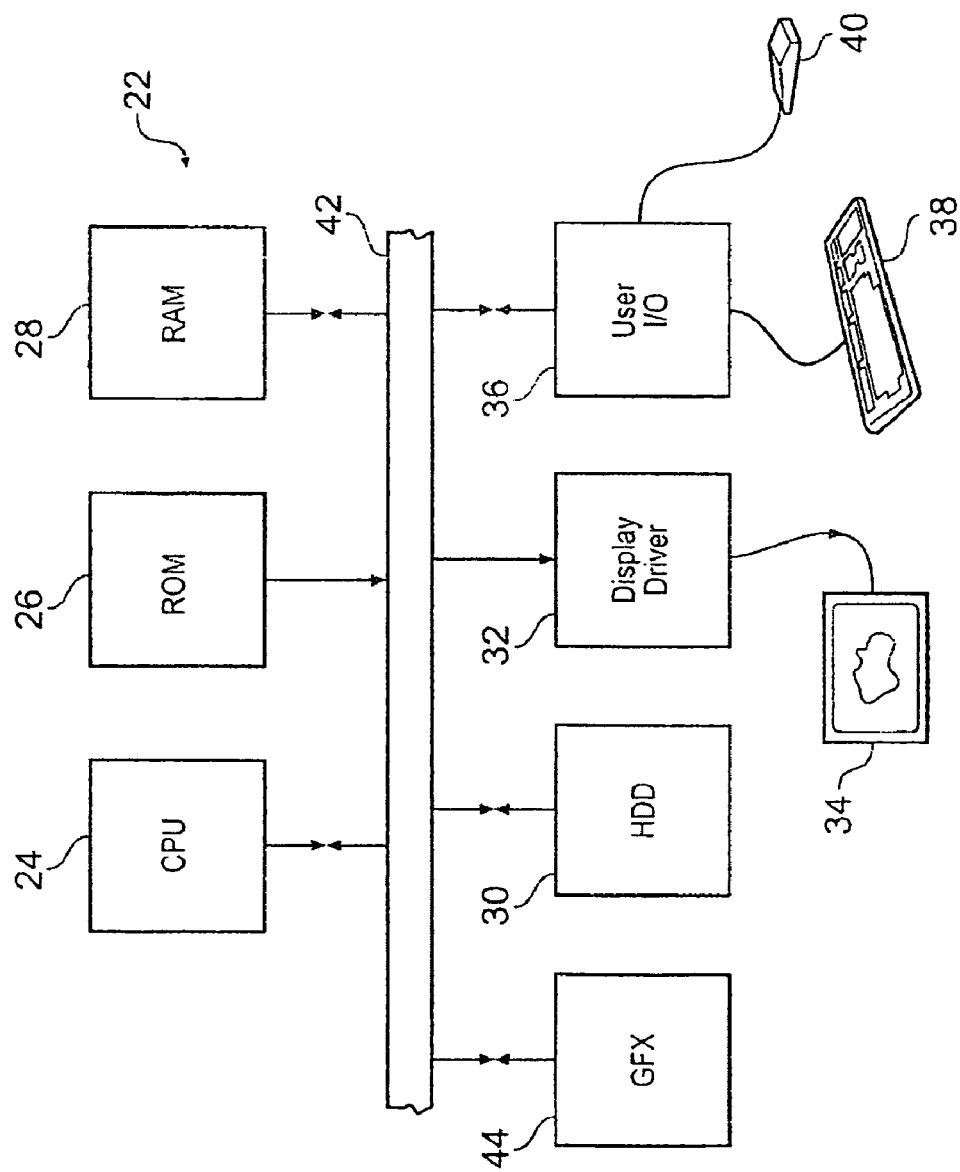
FIG. 2 schematically illustrates a general purpose computer.

FIG. 2 schematically illustrates a general purpose computer system 22 (such as computers 12, 16 or 18 in FIGS. 1A and 1B) configured to perform processing of captured images in accordance with an embodiment of the invention. The computer 22 includes a central processing unit (CPU) 24, a read only memory (ROM) 26, a random access memory (RAM) 28, a hard disk drive (HDD) 30, a display driver 32 and display 34, and a user input/output (I/O) circuit 36 with a keyboard 38 and mouse 40. These devices are connected via a common bus 42. The computer 22 also includes a graphics card 44 connected via the common bus 42. The graphics card includes a graphics processing unit (GPU) and random access memory tightly coupled to the GPU (GPU memory) (not shown in FIG. 2).

The CPU 24 may execute program instructions stored in the ROM 26, in the RAM 28 or on the hard disk drive 30 to carry out processing of captured images, for which associated data may be stored within the RAM 28 or the hard disk drive 30. The RAM 28 and hard disk drive 30 are collectively referred to as the system memory. The GPU may also execute program instructions to carry out processing of captured image data passed to it from the CPU.

Figure 3:
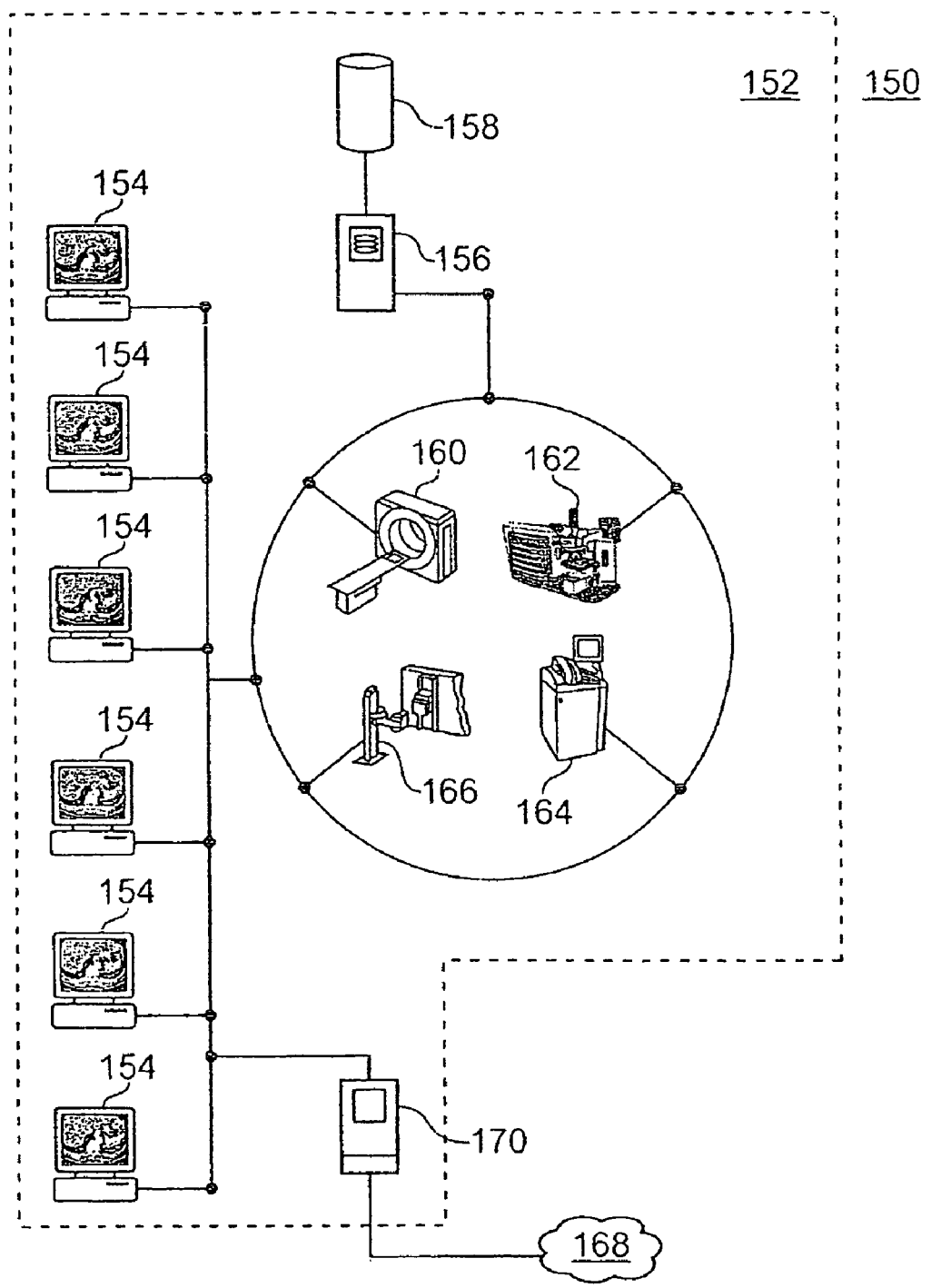
FIG. 3 schematically illustrates a hospital intranet connected to the internet.

FIG. 3 shows an example computer network which can be used in conjunction with embodiments of the invention. The network 150 comprises a local area network in a hospital 152. The hospital 152 is equipped with a number of workstations 154 which have access, via a local area network, to a hospital computer server 156 having an associated storage device 158. A PACS archive is stored on the storage device 158 so that data in the archive can be accessed from any of the workstations 154. One or more of the workstations 154 has access to a graphics card and to software for computer implementation of methods of client-side multi-component image composition as described hereinafter. The software may be stored locally at each workstation 154, or may be stored remotely and downloaded over the network 150 to a workstation 154 when needed. Also, a number of medical imaging devices 160, 162, 164, 166 are connected to the hospital computer server 156 and imaging data collected with the devices 160, 162, 164, 166 can be stored directly into the PACS archive on the storage device 156. Of particular interest in the context of the present invention are the captured images from microscope unit 162. The local area network is connected to the internet 168 by a hospital internet server 170, which allows remote access to the PACS archive. This is of use for remote accessing of data and for transferring data between hospitals, for example, if a patient is moved, or to allow external research to be undertaken. One example use would be for a clinician to access and review sample images, such as a pathologist with tissue sample images.

Figure 4:
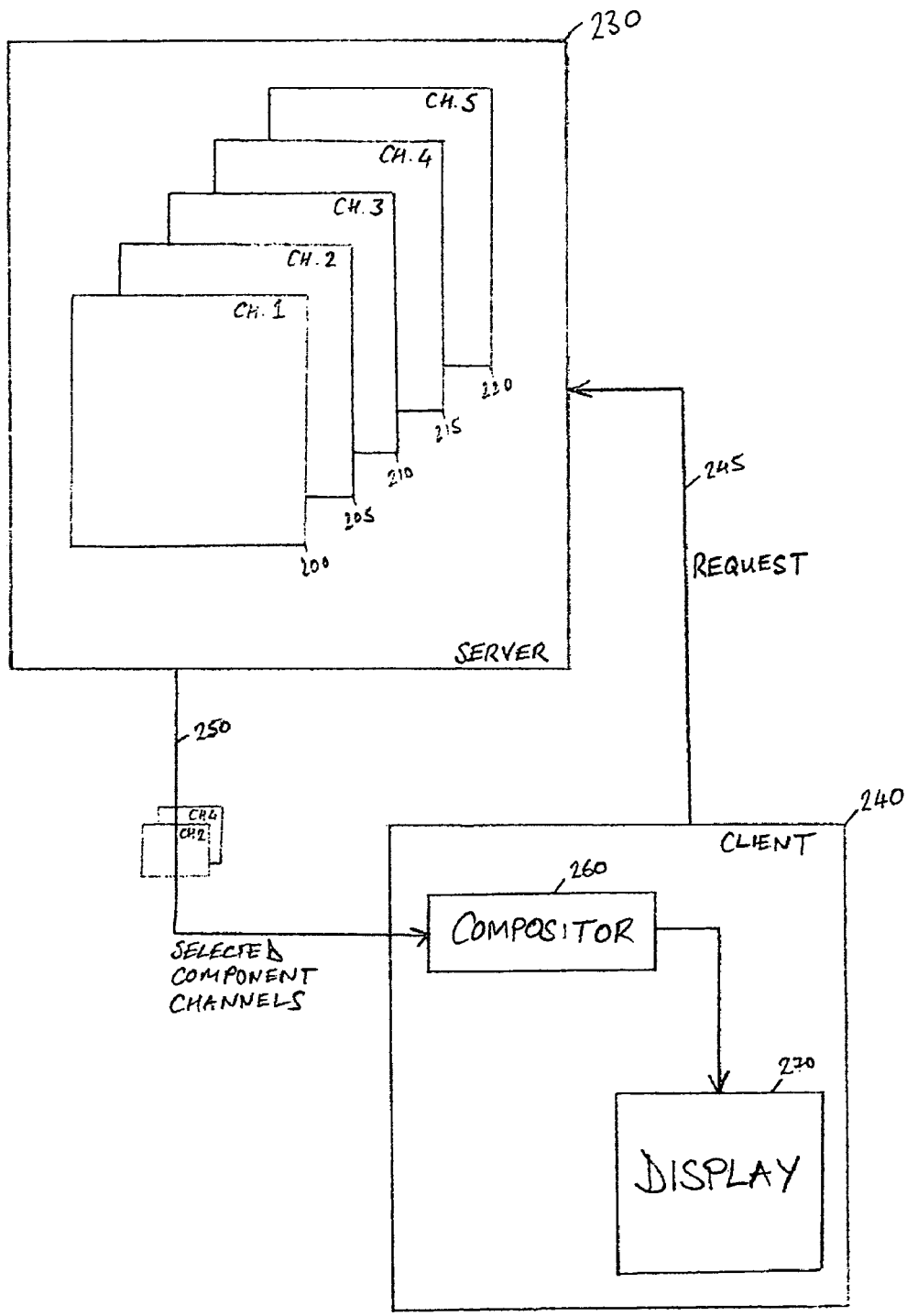
FIG. 4 schematically illustrates a server and client according to one embodiment of the present invention.

FIG. 4 schematically illustrates a server and client according to one embodiment of the present invention. In this embodiment a series of captured images of a sample have been processed and stored as a series of image data records 200, 205, 210, 215, 220 in the server 230. In this example embodiment, image data record 200 (also referred to as channel 1) derives from a bright field captured image of the sample. Image data records 205, 210, 215, 220 derive from a series of fluorescent illuminations of the sample at different wavelengths (also referred to as channels 2, 3, 4 and 5).

Then, client device 240 sends a request to server 230 over request path 245 for image data records to be transmitted over transmission path 250. In this example, client 240 has requested image data records 205 and 215 (i.e. channels 2 and 4), which are then transmitted over transmission path 250. Within the client 240 compositor 260 then combines the image component channels 2 and 4 to generate a client-side multi-component image for display on display unit 270.

Figure 5:
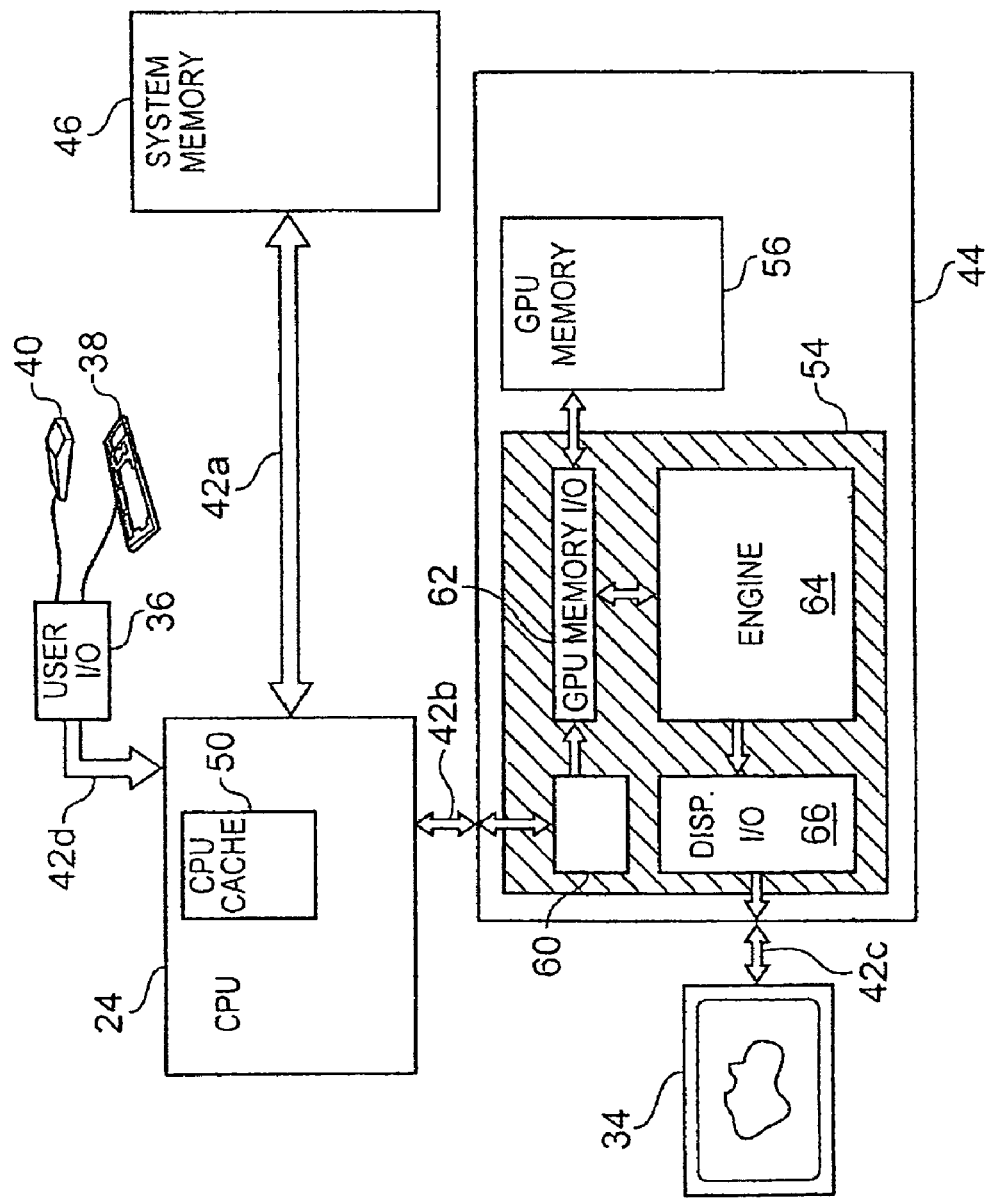
FIG. 5 schematically illustrates a client according to one embodiment of the present invention.

The client device 240 is also a computer system such as that illustrated in FIG. 2 and FIG. 5 schematically shows some of the features of this computer system in more detail. The RAM 28 and hard disk drive 30 are shown collectively in FIG. 5 as system memory 46. The image data records received from the server 230 over transmission path 250 are stored in the system memory 46.

To assist in showing a different data route between features of the computer system 22, the common bus 42 shown in FIG. 2 is schematically shown in FIG. 5 as a series of separate bus connections 42a-d. A first bus connection 42a connects between the system memory 46 and CPU 24. A second bus connection 42b connects between the CPU 24 and graphics card 44. A third bus connection 42c connects between the graphics card 44 and display 34. A fourth bus connection 42d connects between the user I/O 36 and the CPU 24. The CPU includes a CPU cache 50. The graphics card 44 includes a GPU 54 and a GPU memory 56. The GPU 54 includes circuitry for providing an accelerated graphics processing interface 60, a GPU cache I/O controller system 2, a processing engine 64 and a display I/O controller 66. The processing engine 64 is designed for optimized execution of the types of program instructions associated with compositing a multi-component image from received image data records.

The user defines the required parameters using the keyboard 38 and mouse 40 in combination with a menu of options displayed on the display 34, for example using conventional techniques.

Figure 6:
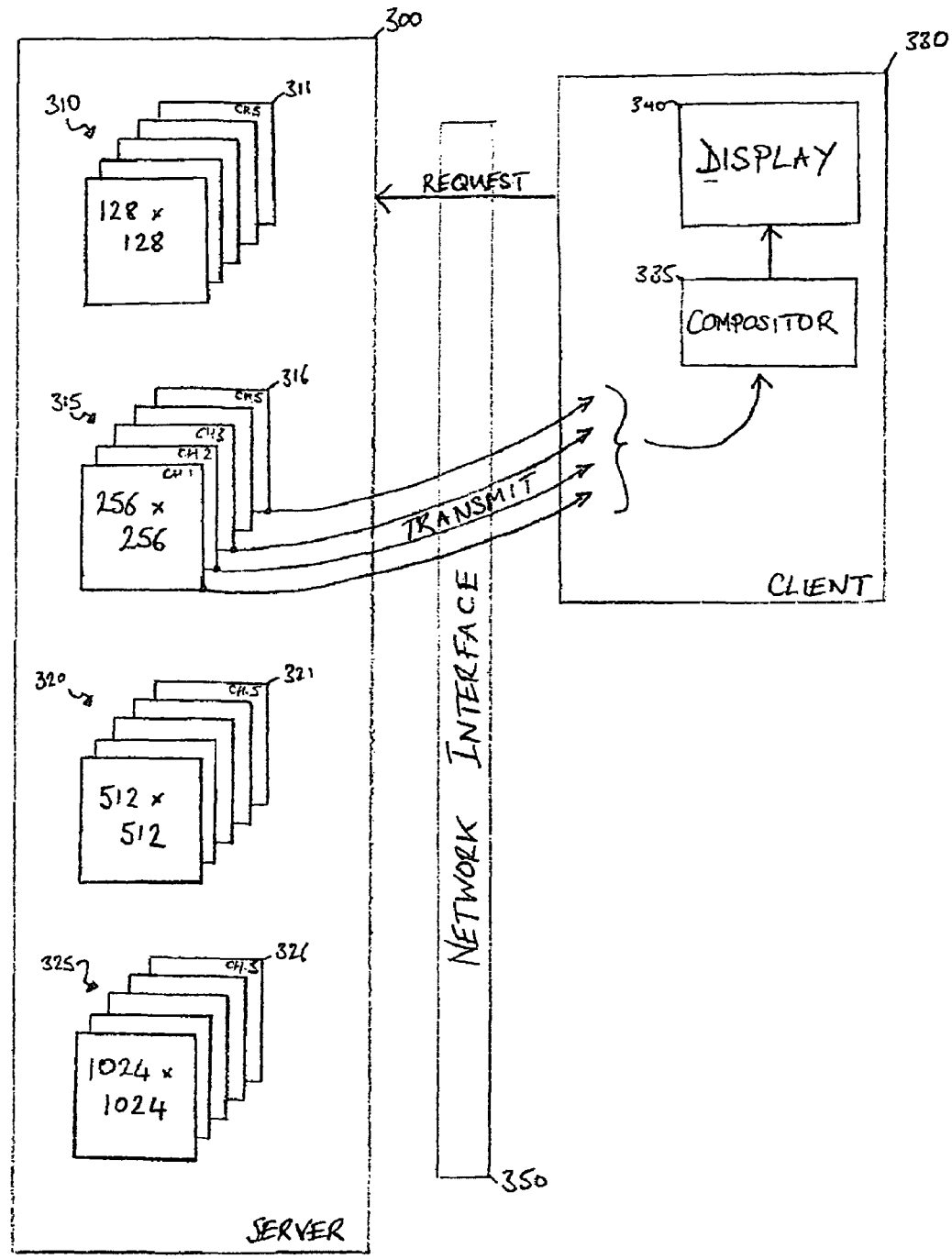
FIG. 6 schematically illustrates a server and client according to one embodiment of the present invention, the server storing a hierarchy of tiles.

FIG. 6 schematically illustrates the server and client accordingly to one embodiment of the present invention. Server 300 stores the image component channels which have been derived from captured images of a sample, these image component channels being stored in the form of image data records. The image data records are stored as a hierarchy of image data records 310, 315, 320 and 325, each level of the hierarchy comprising a set of image data records of a given resolution. In the example embodiment illustrated the set of image data records 310 comprises 128×128 resolution records of each image component channel, the set of image data records 315 being of resolution 256×256, the set of image data records 320 being of resolution 512×512 and the set of image data records 325 being of resolution 1024×1024. Hence stored in the server 300 are a set of image data records of a given resolution for each image component channel (e.g. the set of 256×256 resolution image data records 315) and each image component channel is stored as a set of image data records of progressively increasing resolution (e.g. the channel 5 set of image data records 311, 316, 321 and 326).

The client 330 sends a request to server 300, the request being transmitted via network interface 350, the request specifying both the image component channels required as well as the resolution at which they should be supplied. In the example illustrated channels 1, 2, 3 and 5 at resolution 256×256 are requested and the corresponding image data records are transmitted by server 300 via network interface 350 to the client 330. These image data records received at the client are then composited by a compositor 355 for display on the display unit 340. It will be understood that this compositing will typically be performed by a graphics card such as 44 illustrated in FIG. 5 but for simplicity in this illustration it is only illustrated in its functional role as compositor 335.

The client user operating client device 330, having viewed the composited image at 256×256 resolution, may, for example, then decide to zoom in on the image to examine the sample in greater detail and thus a further request will be transmitted over network interface 350 to server 300, for example requesting the same channel numbers but at resolution 512×512. Equally, the client user could decide to zoom in even further on just one channel, for example requesting only channel 5 at 1024×1024 resolution then being sent image data record 326 over network interface 350.

Figure 7A:
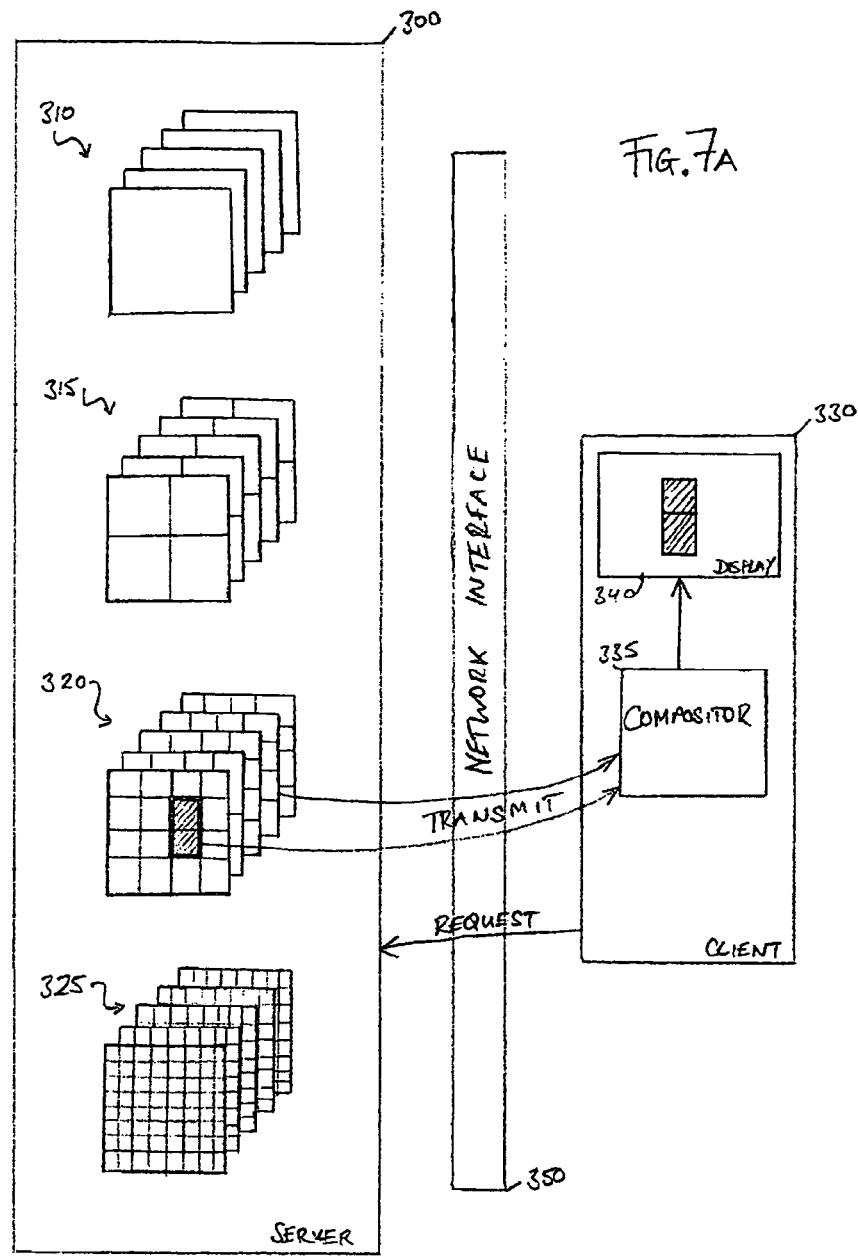
FIG. 7A schematically illustrates a server and client according to one embodiment of the present invention.

FIG. 7A schematically illustrates a further variation on the arrangements schematically illustrated in FIG. 6. In this example embodiment, the hierarchy of image data records 310, 315, 320 and 325 comprises a set of tiles at each level of the hierarchy. Each tile is of the same resolution, in this example being 128×128, but the number of tiles for each image component channel increases as one moves through the hierarchy. Hence each image component channel comprises only one tile at level 310, comprises four tiles at level 315, comprises 16 tiles at level 320 and comprises 64 tiles at level 325. In this example embodiment the client 330 not only requests particular image component channels and resolution, but can further specify which tiles from a given level of the hierarchy are required. As illustrated in FIG. 7A the client has requested two adjacent tiles from level 320 of the hierarchy to be transmitted for two image component channels. These have been received by the client, composited and displayed on display 340.

Figure 7B:
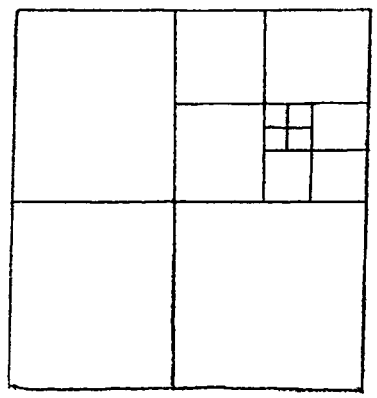
FIG. 7B schematically illustrates nested tiles.

The tiles discussed in relation to FIG. 7A are generated by repeatedly subdividing a tile corresponding to the coarsest level in to four, or more specifically 2×2 sub-units, as is illustrated in FIG. 7B. FIG. 7B illustrates a series of four subdivisions of a tile to produce the set of four smallest tiles illustrated. It will be appreciated that other subdivisions may be used, for example 2×3, 2×4, 3×4 etc. with the choice being up to the designer having regard to the intended uses.

Figure 8:
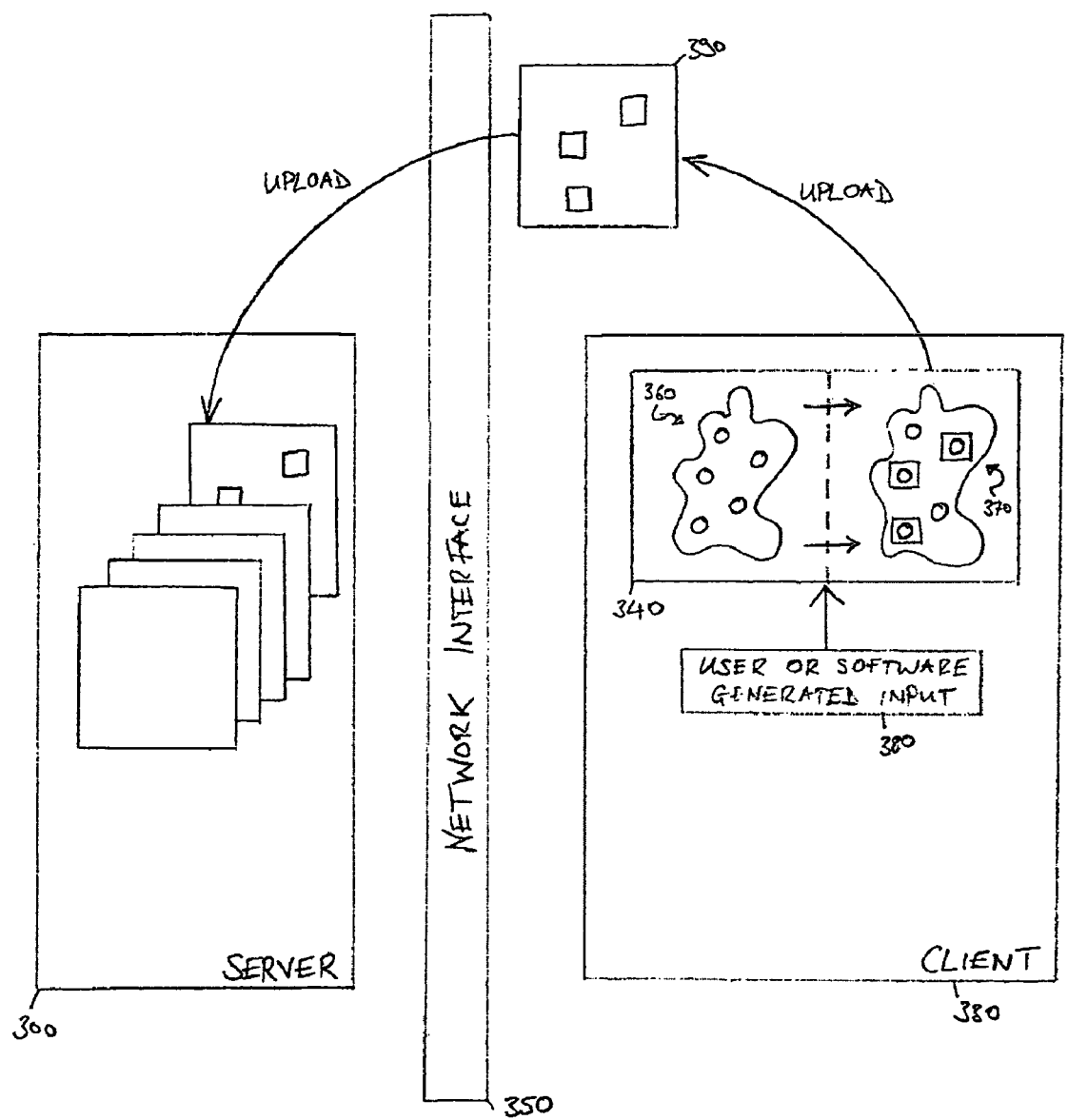
FIG. 8 schematically illustrates uploading analysis results from a client to a server according to one embodiment of the present invention.

FIG. 8 schematically illustrates a further example embodiment of the present invention. In this embodiment it is not only possible for the client 330 to request image data records from the server 300, but also to generate and upload further image data records from the client 330 to server 300. A composited image 360 displayed on display unit 340 of the client 330 is modified to generate modified image 370. This modification may come about either by user or by software generated input as illustrated by item 380. In the illustrated example the modification comprises highlighting three portions of the composited image which are of interest. These could for example represent cells in a tissue sample which are suspected of being cancerous. The client 330 then uploads the corresponding modification information to the server 300 via network interface 350. This modification information 390, in this example in the form of a mask, is then stored in a server as a further image data record. This new image data record is then available both to the uploading client and to other clients which have access to the server 300. Hence for example one client user may identify samples or portions of samples interest and make these available to other users for discussion or confirmation. In the context of FIGS. 1A and 1B, this means that the illustrated line indicating data flow has become bi-directional.

Figure 9:
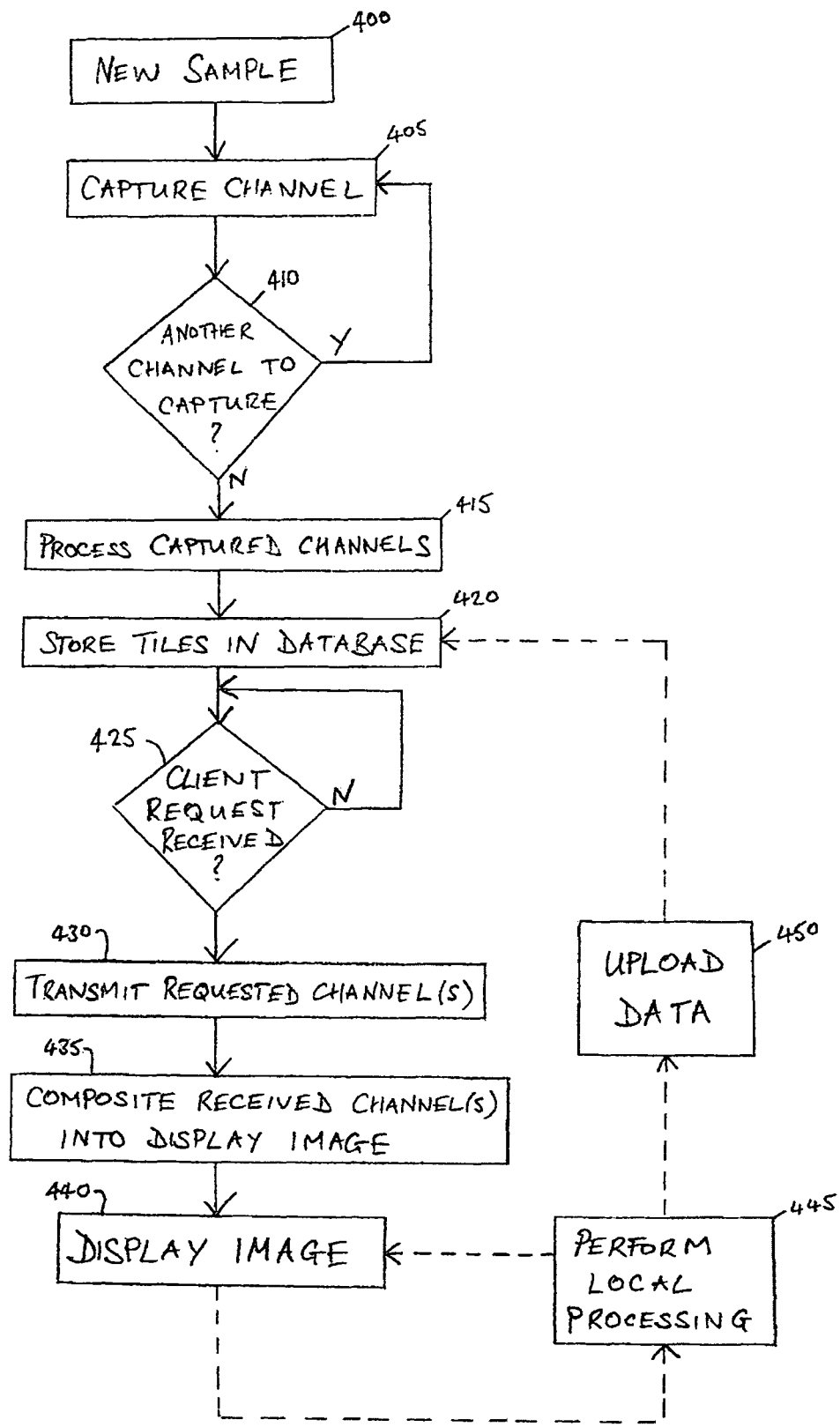
FIG. 9 schematically illustrates a series of steps carried out in one embodiment of the present invention.

FIG. 9 schematically illustrates a series of steps carried out in one embodiment of the present invention. First at step 400 a new sample is ready to be imaged. At step 405 a first image is captured of the sample to provide a first image component channel. For example this could comprise a bright field illumination of the sample. Then at step 410 it is determined if there is another channel to capture of the image. If there is then the flow returns to step 405 and the next image component channel is captured, the flow continuing around this loop until all image component channels have been captured. For example this could comprise illuminating the sample with several different wavelengths of light in succession in order to stimulate various fluorescent in-situ hybridization (FISH) labels in the sample. Once all image component channels have been captured, the flow proceeds to step 415 where the captured channels are digitally processed to convert the camera frame or frames corresponding to each image component channel into tiles to be stored in the server database. Then at step 420 the generated tiles are stored in the database.

The flow then waits at step 425 until a client request is received. On receipt of a client request at step 430 the requested channel or channels are transmitted to the client by transferring the corresponding image data records over the network interface to the client. Then, at the client-side, at step 435 the image component channels (received in the form of image data records) are composited into an image to be displayed and at step 440 that image is displayed at the client-side.

The dashed lines in FIG. 9 illustrate an optional further variation on this embodiment in which the client performs some local processing on the displayed image. This local processing is performed at step 445 after which the flow either returns to step 440 with an updated image to be displayed or if the local processing involves creating a new image data record to be uploaded then at step 450 the result of the local processing is uploaded to the server and at step 420 the uploaded data is stored in the database (in this embodiment as new tiles).

Figure 10:
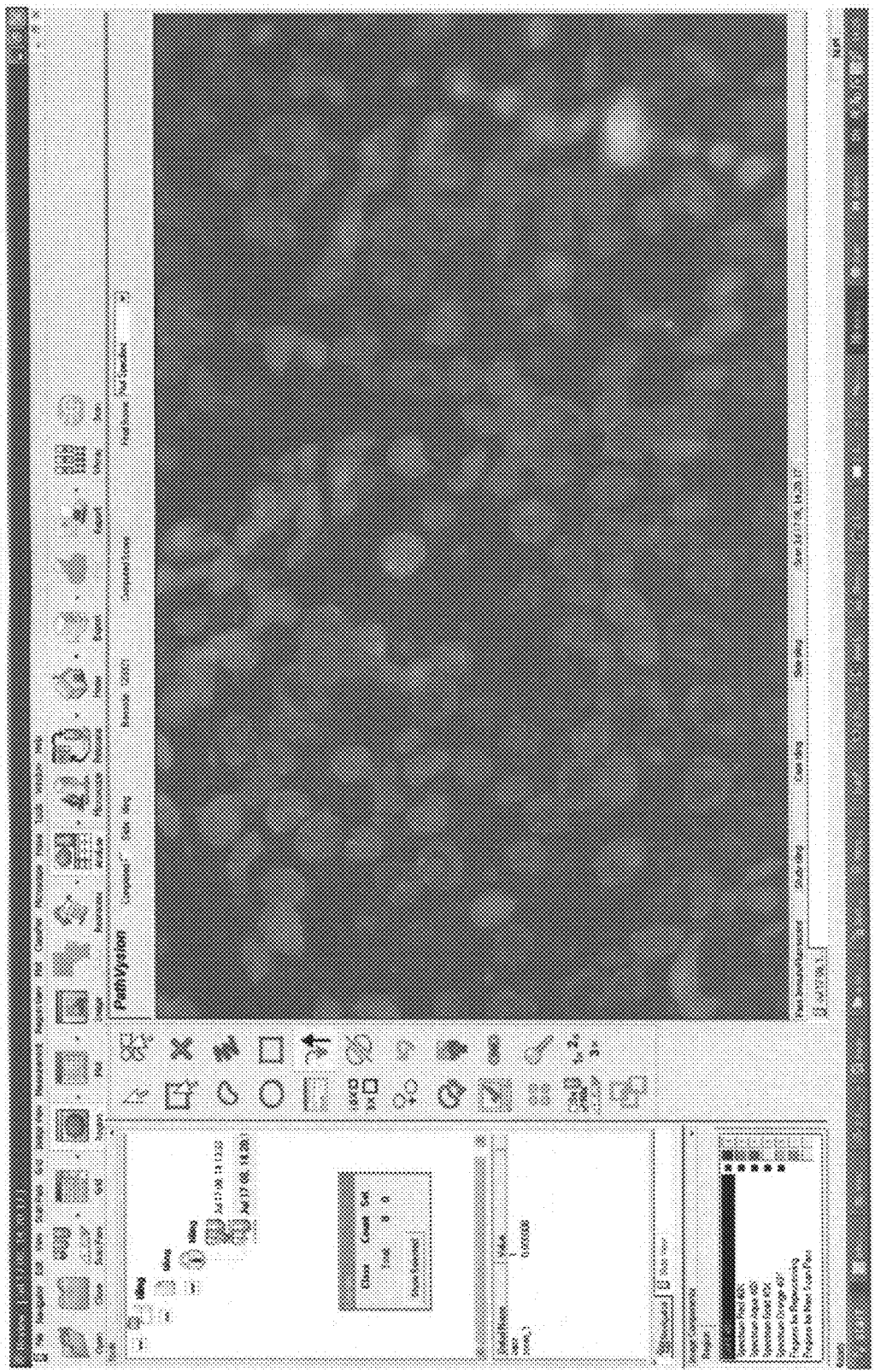
FIGS. 10 and 11 schematically illustrate compositing a client-side multi-component image.

FIG. 10 schematically illustrates a composited client-side multi-component image being displayed on a client display. Here the composited image derives from captured images of a sample of tissue taken from a patient's colon and is being inspected for signs of cancer. This sample has been previously treated with 5 fluorescent in-situ hybridization labels, as well as being DAPI-stained. Images of the DAPI-stained sample (bright field illuminated) and the four FISH labels (illuminated by their appropriate light wavelength) have been separately captured and in the display illustrated in FIG. 10 all five of these image component channels have been combined to produce the composited client-side image. Note the small window lower left in the display in which selected radio buttons indicate that all five image component channels are being displayed.

Figure 11:
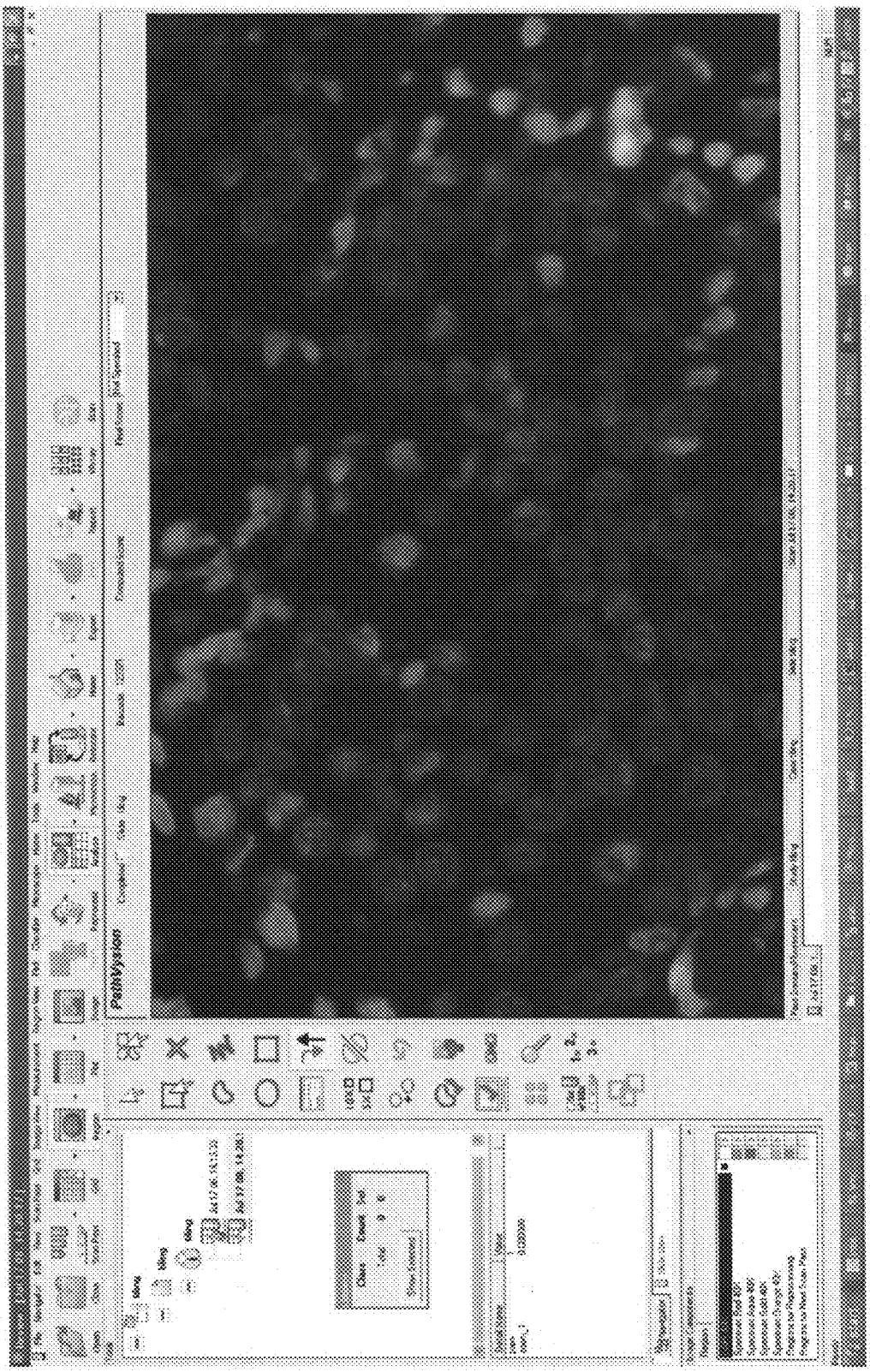

The display illustrated in FIG. 10 may then be compared to the display illustrated in FIG. 11 in which the control panel lower left indicates that the radio buttons for the four FISH component channels have been switched off, leaving only the DAPI component channel being displayed. Thus, by toggling between the image component channels and compositing a new display image at the client-side the client user is presented with a flexible and intuitive means of identifying the contribution to the displayed image of each of the image component channels. Significantly each of the image component channels may be displayed individually at the client-side without loss of information, since they have not been transmitted in a manner which saves transmission bandwidth at the expense of the distinction between individual image component channels.

Figure 12:
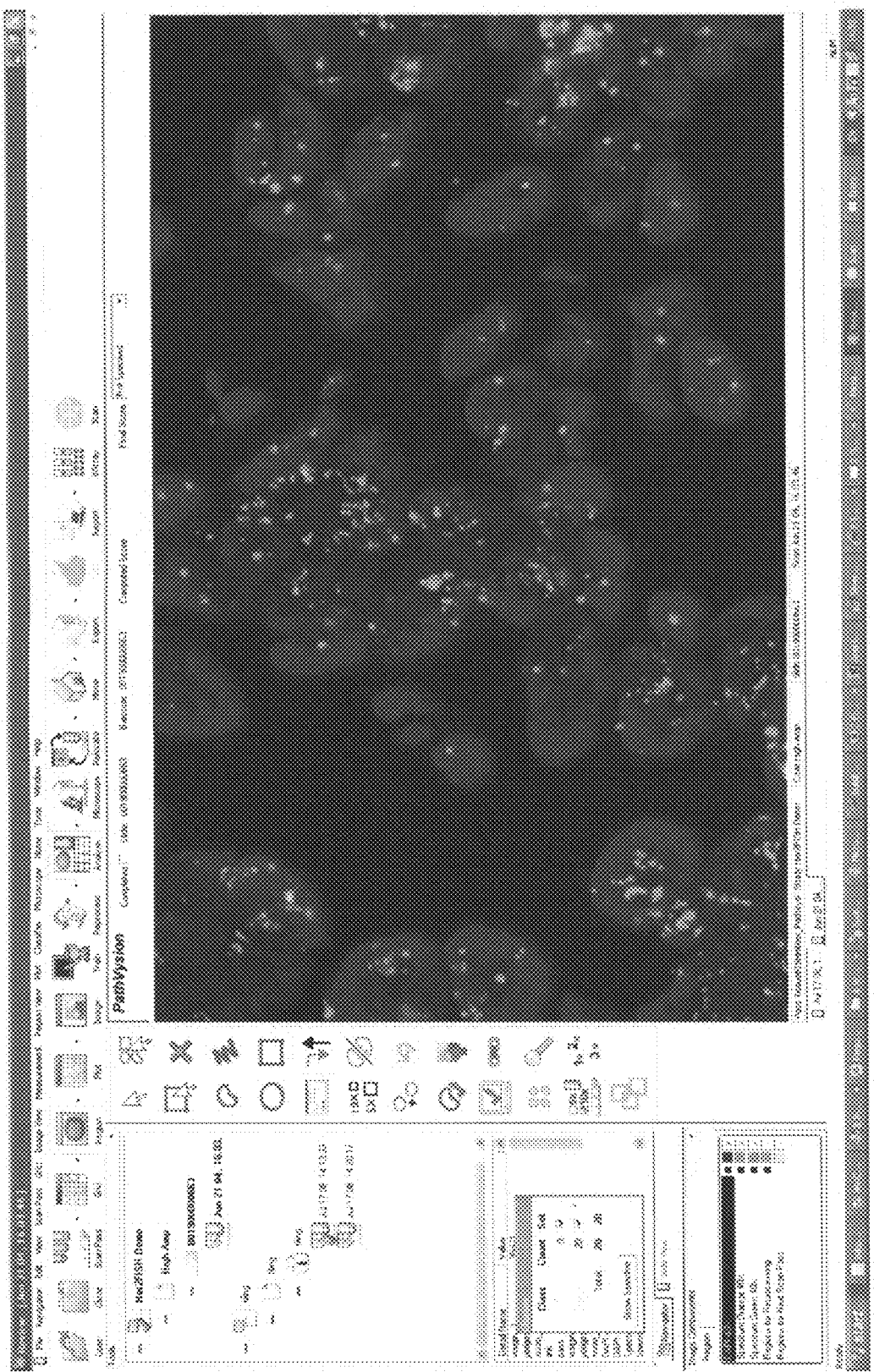
FIG. 12 illustrates a client-side display according to one embodiment of the present invention.

FIG. 12 illustrates a client-side display in an implementation of one embodiment of the present invention. The figure shows a screen shot from a computing system running the Windows operating system of images from a slide that has been labeled using a commercial probe kit and subsequently imaged. In this example, three fluorescent channels have been captured and rendered on the display of the client machine in the application's main window, namely; a counter-stain channel captured from a Dapi filter showing cell nuclei, a test signal channel captured from a Spectrum Orange filter showing the HER2 gene, and a control channel captured from a Spectrum Green filter showing the centromere of chromosome 17. The medical context of this test is to detect amplifications of the HER2 gene with respect to the centromere of chromosome 17 to detect HER2 status in breast cancer.

Although particular embodiments of the invention have been described herein, it will be apparent that the invention is not limited thereto, and that many modifications and additions may be made within the scope of the invention. For example, various combinations of the features of the following dependent could be made with the features of the independent claims without departing from the scope of the present invention.

What is claimed is:

1. A method of displaying a client-side multi-component image, comprising:
   storing in a server a plurality of image component channels, each image component channel being derived from images of a sample captured using illumination of a wavelength different than for the other image component channels, each of said plurality of image component channels being stored in the form of a plurality of image data records;
   requesting by a client two or more of said plurality of image data records corresponding to two or more image component channels;
   transmitting from the server to the client the two or more of said plurality of image data records requested in said requesting step;
   compositing the client-side multi-component image from the two or more of said plurality of image data records transmitted in said transmitting step; and
   displaying the composited client-side multi-component image.

2. A method as claimed in claim 1, wherein
   said plurality of image data records comprises a hierarchy of image data records for each component channel, each level of the hierarchy comprising a set of image data records, each set of image data records comprising image data records having different resolutions from each other; the method further comprising:
   at said requesting step the client specifying a desired resolution; and
   at said transmitting step the server selecting and transmitting image data records appropriate to the desired resolution that has been requested.

3. A method as claimed in claim 1, wherein
   said plurality of image data records comprises a set of tiles for each image component channel, the set of tiles together forming the image component channel, the method further comprising:
   at said requesting step the client specifying a desired portion of the captured images; and
   at said transmitting step the server transmitting image data records appropriate to the desired portion of the captured images.

4. A method as claimed in claim 3, wherein
   said compositing further comprises stitching more than one tile of said set of tiles together to form the composited client-side multi-component image.

5. A method as claimed in claim 1, wherein,
   said plurality of image data records for each image component channel comprises image data records having different focal depths of the captured images, the method further comprising:
   at said requesting step the client specifying a desired focal depth of the captured images; and
   at said transmitting step the server transmitting image data records appropriate to the desired focal depth of the captured images.

6. A method as claimed in claim 1, wherein,
   the image component channels of the captured images are monochromatic.

7. A method as claimed in claim 1, wherein
   the compositing step comprises transforming the one or more of said plurality of image data records transmitted in said transmitting step into an RGB image.

8. A method as claimed in claim 1, wherein
the storing step comprises compressing the captured images using an image data compression protocol and storing the compressed captured images as the image data records, so that each image data record includes a compressed version of the captured images.

9. A method as claimed in claim 1, wherein
the compositing step comprises transforming the one or more of said plurality of image data records transmitted in said transmitting step into a compressed image format.

10. A method as claimed in claim 1, wherein
the captured images are images of a tissue sample.

11. A method as claimed in claim 1, wherein
the captured images are images of a cell mono-layer.

12. A method as claimed in claim 1, wherein
the image component channels of the captured images comprise fluorescent imaging information.

13. A method as claimed in claim 12, wherein
the fluorescent imaging information results from a fluorescent in situ hybridization (FISH) labeled sample.

14. A method as claimed in claim 12, wherein
the fluorescent imaging information results from an immunohistochemistry labeled sample.

15. A method as claimed in claim 1, wherein
the image component channels of the captured images comprise analysis data created after capturing of the captured images.

16. A method as claimed in claim 15, wherein
the analysis data is user-generated.

17. A method as claimed in claim 15, wherein
the analysis data is software-generated.

18. A method as claimed in claim 1, comprising the further steps of:
performing image analysis at the client;
generating additional image information at the client dependent on the image analysis; and
uploading the additional image information as a further image data record to be stored in the server.

19. A client apparatus, the client apparatus configured to:
request from a server two or more of a plurality of image data records stored in the server, the plurality of image data records representing image component channels each image component channel being derived from images of a sample captured using illumination of a wavelength different than for the other image component channels;
receive the two or more of said plurality of image data records transmitted from the server;
composite a client-side multi-component image from the two or more of said plurality of image data records transmitted from the server; and
display the composited client-side multi-component image.

20. A system for displaying a client-side multi-component image, the system comprising:
a client apparatus and a server apparatus,
the client apparatus configured to:
request from a server two or more of a plurality of image data records stored in the server, the plurality of image data records representing image component channels each image component channels being derived from images of a sample captured using illumination of a wavelength different than for the other image component channels;
receive the two or more of said plurality of image data records transmitted from the server apparatus;
composite a client-side multi-component image from the two or more of said plurality of image data records transmitted from the server apparatus; and
display the composited client-side multi-component image;
and the server apparatus configured to:
store the plurality of image component channels in the form of a plurality of image data records;
receive a request from the client apparatus for the two or more of said plurality of image data records; and
transmit to the client apparatus the two or more of said plurality of image data records requested.

* * * * *